United States Patent [19]

Goldberg et al.

[11] Patent Number: 5,352,184

[45] Date of Patent: Oct. 4, 1994

[54] RESERVOIR FOR ENCLOSING AND RETRIEVING BODY SPECIMENS

[75] Inventors: Mark C. Goldberg, Boston, Mass.; Lev Melinyshyn, Buffalo Grove, Ill.; Alexander Poloyko, Morton Grove, Ill.; Edward M. Goldberg, Glencoe, Ill.

[73] Assignee: UreSil Corporation, Skokie, Ill.

[21] Appl. No.: 850,655

[22] Filed: Mar. 12, 1992

[51] Int. Cl.⁵ ............................... A61F 2/00
[52] U.S. Cl. ................ 600/37; 128/DIG. 24; 606/114; 606/127
[58] Field of Search ............... 128/897–899, 128/760, 763, 765, DIG. 24, 749; 600/37; 604/27; 606/114, 127

[56] References Cited

U.S. PATENT DOCUMENTS

| 5,037,379 | 8/1991 | Clayman et al. | 600/37 |
| 5,143,082 | 9/1992 | Kindberg et al. | 600/37 |
| 5,147,371 | 9/1992 | Washington et al. | 606/113 |

Primary Examiner—Lee S. Cohen
Assistant Examiner—John P. Lacyk
Attorney, Agent, or Firm—Marshall, O'Toole, Gerstein, Murray & Borun

[57] ABSTRACT

A specimen-receiving receptacle apparatus for use in minimally invasive surgical procedures can be remotely opened and closed from a proximal end of the apparatus, outside of the patient. The apparatus includes a belt having substantial longitudinal rigidity so that the belt can be forced longitudinally into the surgical site to open the specimen-retrieval receptacle from a remote end of the apparatus. The belt can be longitudinally pulled out of the surgical site to close the specimen-retrieval receptacle from outside of the patient. The belt is relatively flexible or easily deformable along an open end of the receptacle without deforming substantially out of the plane of the open receptacle end. This is achieved by aligning the belt with respect to the open end such that a large dimension of the belt is aligned transverse to the plane of the open receptacle end. In a preferred embodiment, the belt is extruded from nylon and has an elliptical cross-sectional shape.

19 Claims, 3 Drawing Sheets

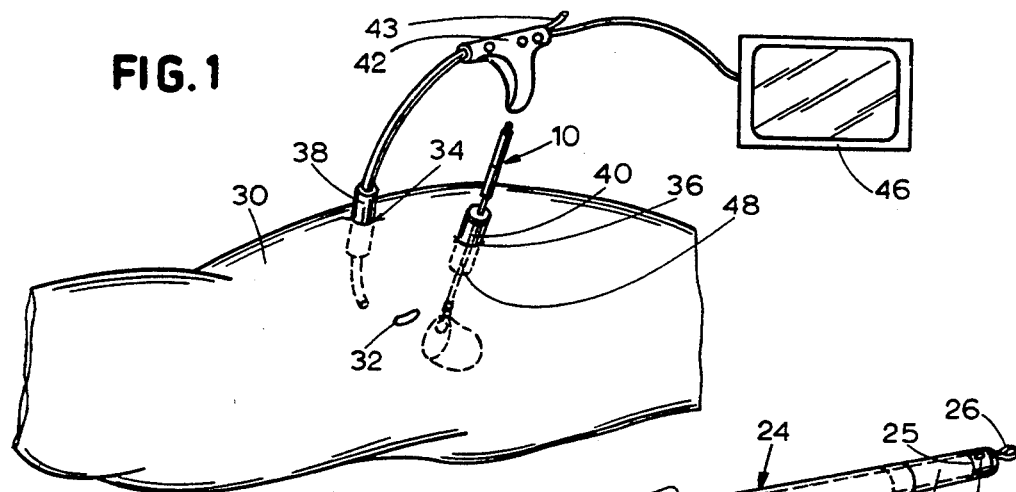
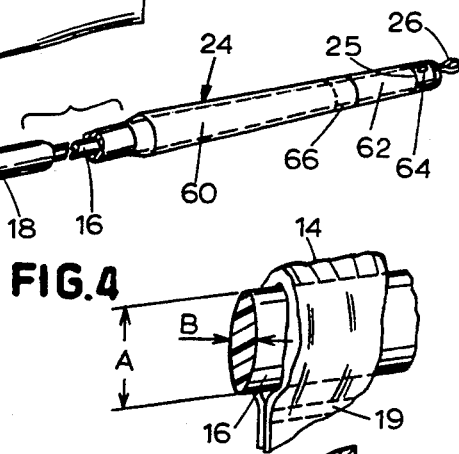
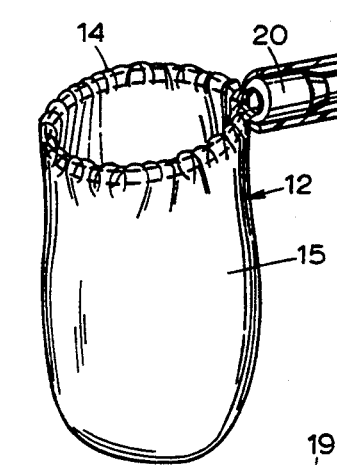
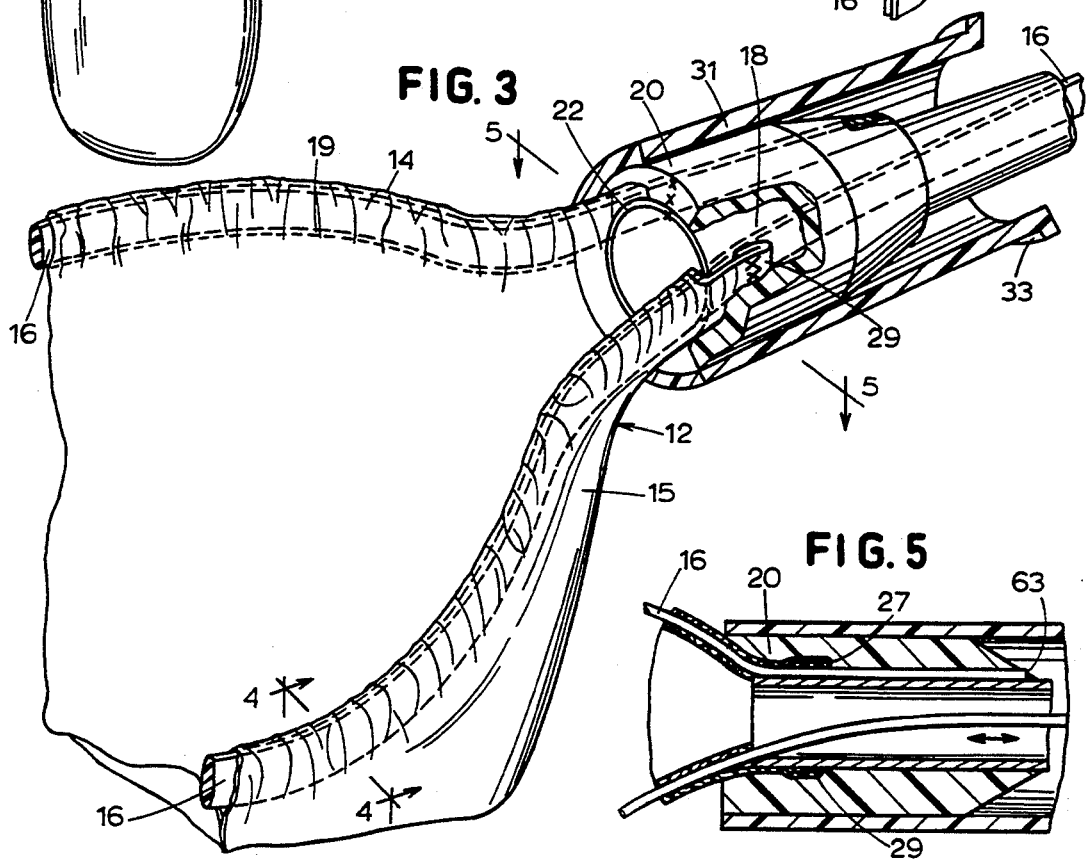
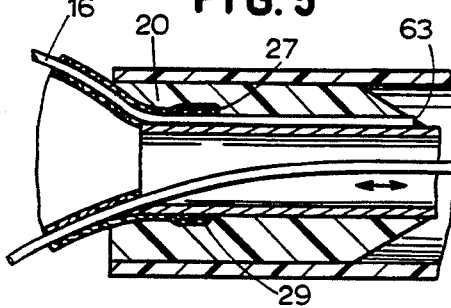

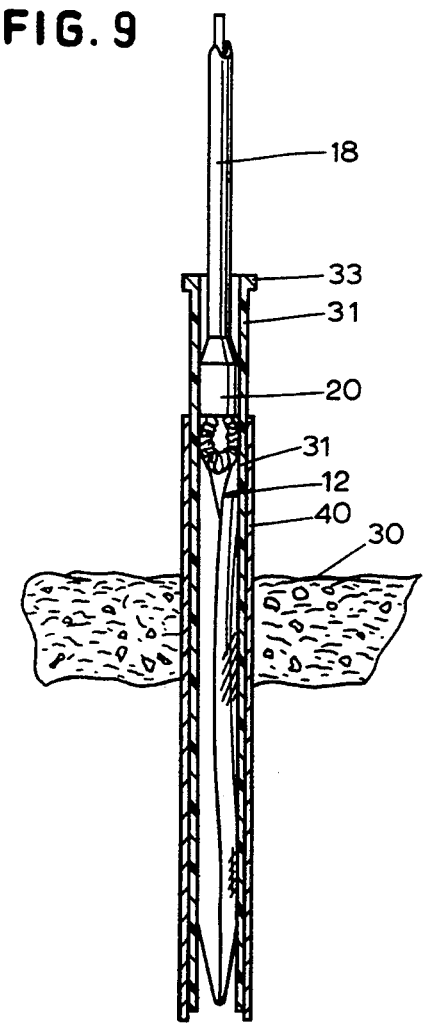
FIG. 9
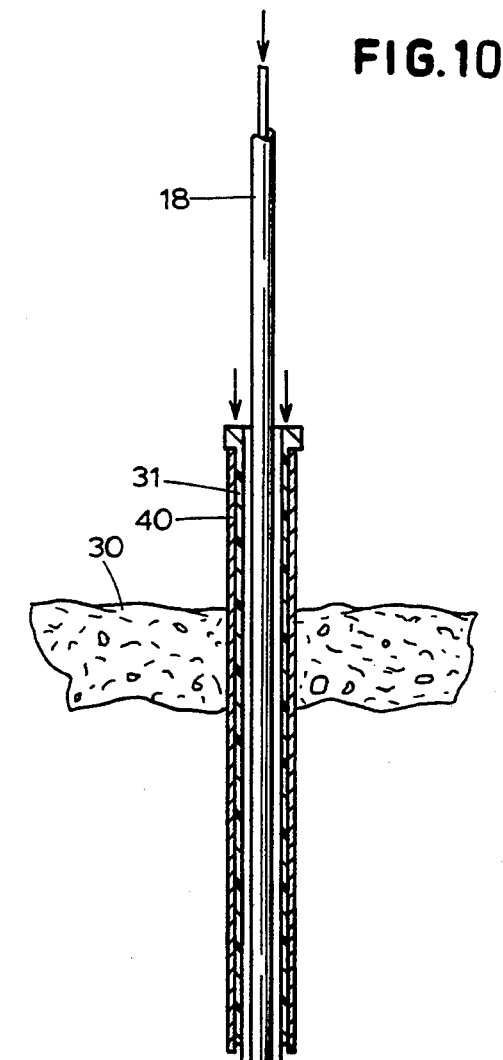
FIG. 10
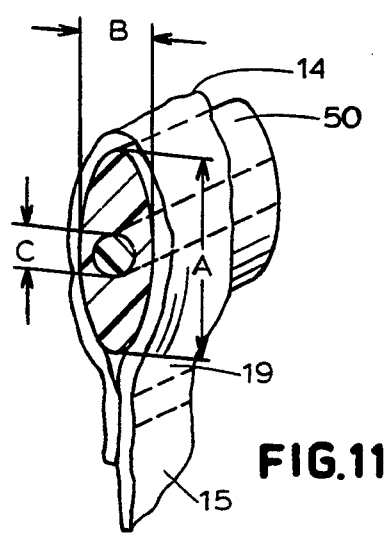
FIG. 11
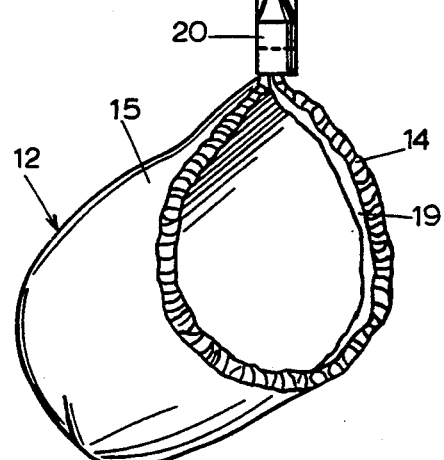

RESERVOIR FOR ENCLOSING AND RETRIEVING BODY SPECIMENS

FIELD OF THE INVENTION

The present invention is directed to a reservoir for receiving and containing physiologic materials from body cavities. The reservoir is introduced through a surgical access port percutaneously inserted into a body cavity and directed to any site in the body cavity. The reservoir can be opened or closed remotely outside or exterior to the body cavity, more particularly, the present invention is directed to a flexible retrieval reservoir that can be remotely opened and closed from outside the body cavity by a control mechanism. This control mechanism can easily open and close the neck of the reservoir and allow the easy introduction of any specimen and the easy sequestration of this material so that it can be easily and safely removed or extracted from the body cavity. The ability to easily remotely open the reservoir is essential to the surgeon because his ability to move instruments and specimens is difficult and limited. The ability to easily remotely close the reservoir is just as essential to avoid contamination from the sequestered specimen. Many of the specimens are fragile, infected, chemically noxious, or malignant. Properly encapsulating the specimen in a closed reservoir is essential in preventing infections, chemical damage and malignant spread.

BACKGROUND OF THE INVENTION AND PRIOR ART

The advantages of minimally invasive endoscopic surgical procedures are well documented throughout the literature. They require substantially smaller incisions that are less traumatic to the patient resulting in accelerated patient recovery and convalescence. Many body cavities can be entered through small incisions by utilizing fiber optic visual systems and special surgical instruments. Thoroscopy, arthroscopy, cystoscopy and laparoscopy are some of the most common of these surgical procedures. One of the most common endoscopic surgical procedures is laparoscopic surgery. The abdominal wall is pierced with a trocar assembly including a sharp trocar within a hollow tube or access port. Multiple other ports are utilized, depending on the operative requirements, to introduce various other devices, including a light source and optical instruments to visualize the operative field and for the purpose of completing the surgical procedure.

Many times during the course of such an endoscopic surgical procedure, specimens must be removed from the patient's body through the relatively small incision. For this purpose, the specimen to be removed must best be captured in a reservoir so that it can be sequestered. Many of these specimens are noxious and should be properly encapsulated or enclosed to prevent contamination as they are removed through the body cavity incision.

The Wilk patent discloses a device that is extremely difficult to operate because it requires the opening of a relatively large planar sheet or membrane in an unstable area. This requires the sheet to be located on shifting organs. Also, the device disclosed in the Wilk patent does not have the capacity to easily remotely open or close the specimen collector. The Wilk device requires the surgeon to open a planar sheet in the body cavity, with extreme difficulty, with other instruments. The planar sheet has no integral mechanism to remotely open the sheet. Rather, it requires other instruments to perform this function and is not remotely controllable.

Surgical specimen receptacles for use in endoscopic surgical procedures are known in the art, as shown in the Clayman, et al. U.S. Pat. No. 5,037,379, where one is formed from a thin polymeric sheet material having a drawstring secured to an open end of the receptacle for the purpose of closing the receptacle around the specimen or other specimen to be removed. The receptacle is closed by pulling on the drawstring from a proximal location outside of the body cavity. Such specimen receptacles or surgical specimen bags are made from a readily collapsible sheet material so that the receptacle can be easily collapsed into a much smaller volume for insertion through the access port. The surgical receptacle sheet material should be a material that is non-porous, flexible and tear resistant. Often times the specimen to be removed is a diseased organ, such as an acute appendix, that contains a substantial amount of infectious fluid. For this purpose, the receptacle should have a remotely and easily controllable entry port that allows quick and easy introduction of the specimen without unwanted manipulation of the receptacle and the specimen. It further requires an easy remote control to encapsulate and enclose the specimen so it can be removed from the body cavity without contamination.

One of the problems associated with prior art endoscopic surgical specimen receptacles used in minimally invasive surgical procedures is that opening of such a receptacle in a body cavity requires manipulation of the receptacle with a surgical tool inserted in the body cavity through another access port. The additional effort in such a procedure may be eliminated in accordance with the principles of the present invention.

SUMMARY OF THE INVENTION

An endoscopic minimally invasive specimen-retrieval apparatus is manufactured in accordance with the principles of the present invention so that the receptacle, after closure, can be integrally and remotely opened and closed from a proximal end of the apparatus, outside of the patient.

Instead of employing a relatively limp drawstring closure, such as disclosed in Clayman, et al. U.S. Pat. No. 5,037,039, the apparatus of the present invention includes an elongate belt received within a tube having substantial longitudinal rigidity so that the tube can be directed longitudinally into the surgical site. The belt may be used to both close and alternately open the specimen-retrieval receptacle from a proximal end of the apparatus. The belt is relatively easily flexed around an open neck of the receptacle without bending substantially out of a plane of the open receptacle end by aligning the belt material with respect to the open receptacle end such that a larger or major axis of the belt is aligned perpendicular to the plane of the open receptacle end. In a preferred embodiment, the belt is extruded from nylon to have an elliptical cross-sectional shape with its major axis disposed perpendicular to the plane of the open receptacle end.

Accordingly, one aspect of the present invention is to provide an improved method and apparatus including a specimen-retrieval receptacle for containing and removing specimen from a patient during a minimally invasive surgical procedure wherein the receptacle can be easily remotely opened from outside of the body.

Another aspect of the present invention is to provide an improved method and apparatus for removing specimens from a surgical site during a minimally invasive surgical procedure wherein specimen, a diseased organ and/or infected or diseased body products can be removed from a body cavity of a patient by closing a specimen-retrieval receptacle about the material to be removed without the manipulation of receptable opening tools within the patient at the surgical site.

BRIEF DESCRIPTION OF THE DRAWING

The above and other aspects, advantages and novel features of the present invention will become apparent from the following detailed description of the preferred embodiment taken in conjunction with the following figures of the drawing.

FIG. 1 is an elevational view showing minimally invasive laparoscopic surgery being performed on a patient using the method and apparatus of the present invention;

FIG. 2 is an enlarged, perspective view of the apparatus of the present invention;

FIG. 3 is enlarged, fragmentary perspective view of a portion of the apparatus of FIG. 2;

FIG. 4 is a detail view taken along the line 4—4 of FIG. 3 showing an elliptical cross-sectional shape of a belt portion of the device of FIG. 3;

FIG. 5 is a fragmentary, broken-away view showing the securement of hemmed receptacle ends and securement of one belt end to the apparatus, taken along line 5—5 of FIG. 3.

FIG. 9 is a fragmentary, broken away perspective view of the device of FIG. 2 positioned in an introducer sleeve, within an access port;

FIG. 10 is a view, similar to FIG. 10, depicting the device of FIG. 2 in a deployed condition inside a body cavity; and FIG. 11 is a partially broken-away perspective view taken along the line 4—4 of FIG. 3 showing an alternative coextruded embodiment of the elliptical belt of the apparatus of FIG. 2.

DETAILED DESCRIPTION OF THE PREFERRED EMBODIMENT

Figure 6:
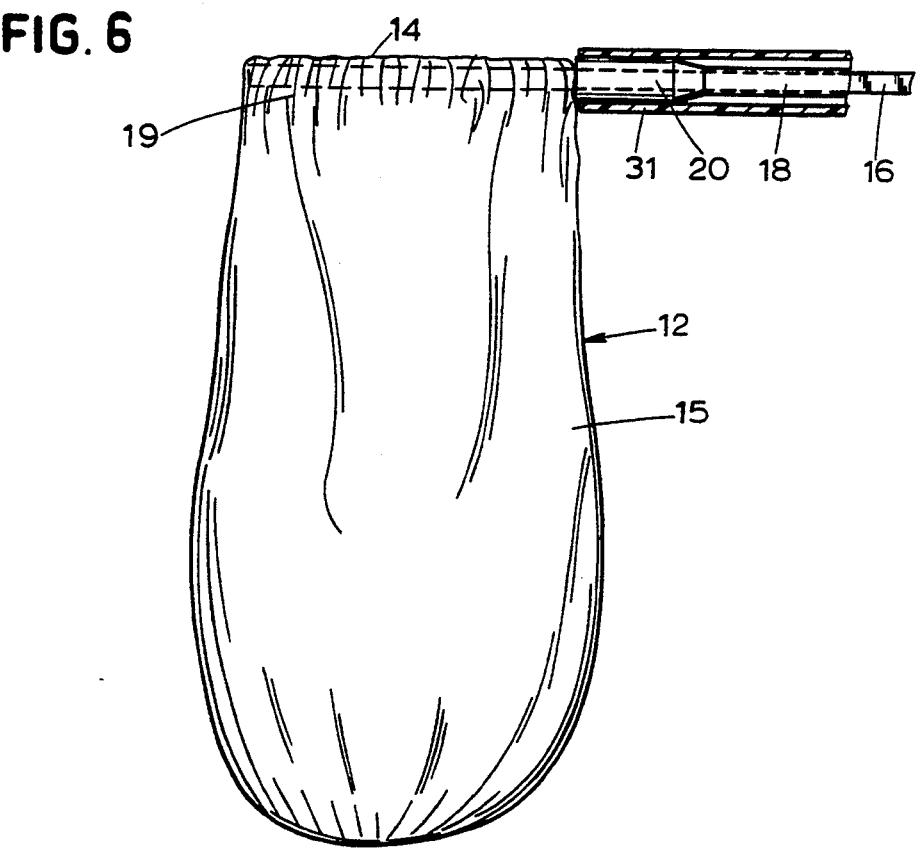
FIG. 6 is a fragmentary side elevational view of the specimen receptacle portion of the apparatus of FIG. 2.
Figure 7:
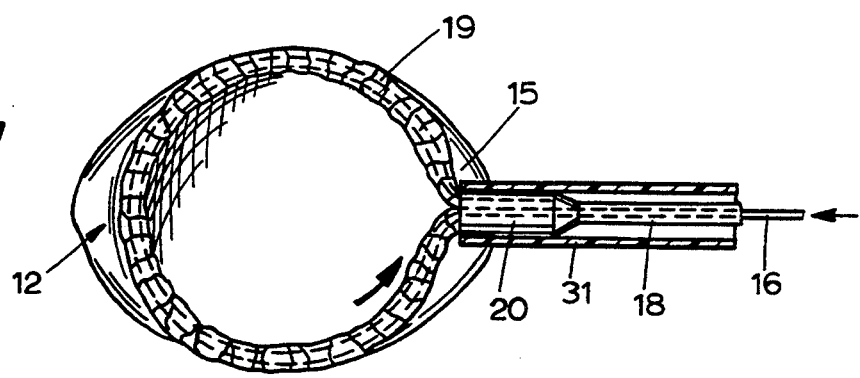
FIG. 7 is a fragmentary top view showing the receptacle portion of the apparatus of FIG. 2 in an open position.
Figure 8:
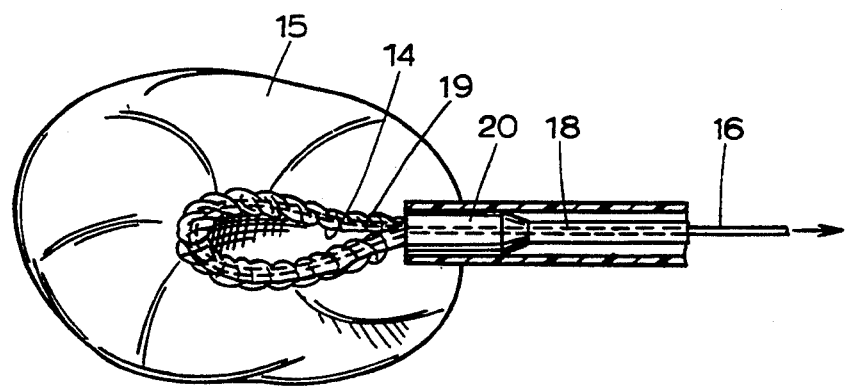
FIG. 8 is a fragmentary top view showing the receptacle portion of the apparatus of FIG. 2 in a closed position.

In accordance with the principles of the present invention, a specimen-receiving apparatus 10 (FIGS. 1-3) includes a flexible receptacle 12 manufactured from a waterproof, flexible and tear resistant material, such as nylon. The receptacle 12 has an open end or neck 14 and an elongate, generally tubular, sealed specimen-retaining receptacle portion or bag 15 extending therefrom. The apparatus 10 also includes an operating belt 16, for opening and closing the end 14, slidably secured to the open end 14 of the receptacle 12. A rigid guide tube 18 is used to guide and constrain the belt 16 from a proximal location outside of the patient's body, along and through the guide tube 18, into a hemmed portion 19 of the open end 14 of receptacle 12. A collar 20 is disposed about a distal end 22 of the guide tube 18 for fixedly securing a distal end 63 of the belt 16 to the guide tube 18 such that a major axis or larger dimension A of the belt 16 (FIG. 4) is maintained transverse to the plane of the open end 14 of receptacle 12. A handle 24 (FIG. 2) is telescopically and slidably received over a proximal end 25 of the guide tube 18, and is fixedly secured to a proximal end 26 of the belt 16. Sliding movement of the handle 24 over guide tube 18 in a distal direction toward the receptacle 12 pushes the belt 16 in a distal direction (FIG. 6) within guide tube 18, thereby lengthening the portion of the belt 16 extending in a distal direction beyond the distal end 22 of guide tube 18. That additional elongate portion of the belt 16 is slidingly received within the hemmed portion 19 at the open end 14 of receptacle 12 to open the receptacle 12 (FIG. 7). Movement of the handle 24 in an opposite direction closes the specimen receptacle 12 (FIG. 8).

To prevent the hemmed portion 19 of the receptacle material from remaining bunched together after closing, one or both hemmed ends 27 and 29 of the receptacle 12 can be secured to the guide tube 18 or to the collar 20, for example, by frictionally securing the hemmed ends 27 and 29 between the guide tube 18 and the collar 20, as shown in FIG. 3. An introducer sleeve 31, surrounding the collar 20 and a portion of the guide tube 18, receives the receptacle 12 and a portion of the belt within hemmed receptacle portion 19 in a collapsed position, having at least a partially closed neck for initially inserting the receptacle 12 through an access port and into the body cavity at a surgical site. Alternatively, the receptacle 12 may be initially disposed in the introducer sleeve 31 in a closed condition. After insertion into the body cavity through the introducer sleeve disposed in the access port, the receptacle 12 may be fully opened by the belt 16 as described above.

FIG. 1 depicts a patient 30 undergoing laparoscopic surgery to remove a diseased organ or other specimen 32 using the apparatus 10 of the present invention. In accordance with the endoscopic minimally invasive surgical procedure of the present invention, after pressurization of the abdomen, trocar assemblies (not shown) are used to make perforations or incisions in the abdomen of patient 30 at trocar sites 34 and 36. Hollow tubular access ports 38 and 40 are installed during the perforation procedures and extend into the abdominal cavity or other body cavity. As shown in FIG. 1, initially an endoscope 42 is inserted through the first access port 38 to provide light transmitted through an optical fiber 43 and images for display on the monitor 46.

The apparatus 10 of the present invention may be inserted through a subsequently formed access port 40 for retrieval of one or more specimens 32. For the performance of laparoscopic surgery, access port 38 generally includes a conventional housing valve assembly connected to a carbon dioxide source (not shown) for maintaining pressurization of the abdominal cavity.

After installation of the access port 40 into a body cavity at the surgical site, the receptacle 12 is inserted into the body cavity therethrough. Prior to insertion into the access port 40, the open end 14 of the receptacle 12 preferably is partially closed and the tubular receptacle portion 15 is collapsed on itself to fit within the introducer sleeve 31 (FIG. 9). The sleeve 31 with the collapsed, and partially closed receptacle 12 disposed therein can be manually directed into the access port 40. By providing the sleeve 31 with a integral annular stop or shoulder 33 extending laterally from sleeve 31, the introducer sleeve 31 is prevented from extending beyond a distal end 48 of the access port 40. The shoulder 33 prevents the sleeve 31 from entering the body cavity by contact with the proximal end 35 of the access port 40. The introducer sleeve 31 also seals the port 40 from excessive loss of pressurization during insertion of the receptacle 12 into the body cavity. The receptacle 12 and the guide tube 18 then can be manually forced through the access port 40 into the surgical site of specimen 32, as shown in FIGS. 1 and 4, while retaining the introducer sleeve 31 within the access port 40. During insertion of the receptacle 12 and the guide tube 18 into the body cavity, the guide tube 18 moves longitudinally with respect to the introducer sleeve shoulder 33 and the shoulder 33 remains stationary in contact with proximal port end 35.

The receptacle portion 15 of receptacle 12 may be manufactured from a minimally biologically intrusive material having sufficient flexibility. One material that is particularly suitable is thin nylon material, for example, nylon 6, 6/6, 6/12 or 12/12. When the receptacle 12 emerges from the distal end 48 of access port 40, within the patient 30, the receptacle 12, under the influence of the expanding belt 16, expands to its operational, generally tubular receptacle shape, as shown in FIGS. 2, 6 and 10. In accordance with an important feature of the present invention, the end 14 of receptacle 12 can be opened within the patient 30 without the necessity of the surgeon inserting receptacle-opening manipulating tools through another incision in patient 30.

After opening of the receptacle 12, the open end 14 of the receptacle 12 is loaded with the specimen 32. The specimen 32 may be placed into the receptacle 12 and then the receptacle 12 is closed about the specimen, e.g., or organ 32 by pulling the handle 24 in a proximal direction, thereby drawing a portion of the belt 16 back into the guide tube 18 to close the receptacle 12.

The guide tube 18 and receptacle 12 then may be pulled outwardly in a proximal direction through the access port 40 for removal of specimen 32 from the patient 30. If the specimen 32 is too large to be removed from the patient 30 through the access port 40, the access port 40 first may be removed prior to the removal of the specimen-containing receptacle 12 and, if necessary, the incision at trocar site 36 can be minimally enlarged. Alternatively, the receptacle can be reopened while still in the body cavity and the specimen 32 may be subdivided while in the receptacle 12 and, if desired, a portion or all of the subdivided specimen can be aspirated out of the receptacle 12 prior to removal of the receptacle 12 from the body cavity of the patient 30.

In accordance with an important feature of the present invention, the belt 16 is manufactured from a material such as nylon, e.g., nylon 6, 6/6, 6/12 or 12/12, in the form of an elongate belt having substantial rigidity in a longitudinal direction while being relatively flexible and easily flexed around the open end 14 of receptacle 12, as shown in FIG. 3. Substantial rigidity in the longitudinal direction enables the belt 16 to be lengthened about the open end 14 of receptacle 12 by pushing handle 24 in a distal direction. The flexibility and capability of relatively easily flexing around the open end 14 of the receptacle 12 permits the belt 16 to slide easily within the hemmed portion 19 of the receptacle 12.

The belt 16 is configured to prevent substantial flexing out of a plane defined by the open end 14 of receptacle 12. This resistance to flexing is achieved, in a preferred embodiment, by manufacturing the belt 16 with an elliptical cross-sectional shape, having a major axis or larger dimension A and a minor axis or smaller dimension B (FIG. 4), and by maintaining the belt 16 within the hemmed portion 19 at the open end 14 of receptacle 12 such that the major axis A is aligned or transverse to the plane passing through the open end 14 of the receptacle 12. Dimension A preferably is at least approximately 50% greater than the dimension B, and more preferably in the range of about 75% to about 150% greater than dimension B. For example, in the preferred embodiment, dimension A is approximately 0.080±0.005 inch and dimension B is approximately 0.040±0.005 inch. The aforementioned alignment and relative dimensions of belt 16 within the hemmed portion 19 of open end 14 of receptacle 12 provides the belt 16 with substantial resistance to flexing in a direction normal to the plane of the open end 14 while permitting the belt 16 to be relatively easily flexed in a direction parallel to the plane of the end 14, for receptacle opening and closing operations, respectively.

In a preferred embodiment, the belt 16 is extruded from nylon or other polymeric material having a relatively low coefficient of friction and in an elliptical cross-sectional shape, as shown in FIG. 4. The elliptical exterior surfaces of the belt 16 preferably have no sharp corners in contact with inner surfaces of the hemmed receptacle portion 19 to achieve low friction sliding engagement of the belt 16 through the hemmed portion 19 during opening and closing of receptacle 12.

In accordance with another embodiment of the present invention, as shown in FIG. 11, an alternative belt 50 having an elliptical cross-sectional shape including a major axis or larger dimension A and a minor axis or smaller dimension B, preferably dimensioned as described above with reference to FIG. 4, is manufactured by coextruding a polyurethane material 52 about a nylon core 54. The interior nylon core 54, having a circular cross sectional shape provides rigidity, while the polyurethane material 52 provides flexibility and a low coefficient of friction to the exterior of the belt 50. The dimension C or diameter of the core 54, relative to the B dimension is preferably about one-half of the B dimension, or in a specific example, in the range of from about 0.020 to about 0.025 inch while the other relative dimensions A and B may be the same as recited hereinabove with respect to FIG. 4.

As shown in FIG. 2, the handle 24 may be manufactured in two interlocking parts, a distal portion 60, and a proximal portion 62 that interlock over guide tube 18 during manufacture of the apparatus 10. During manufacture, the belt 16 is secured at the distal end 63 to the guide tube 18 under collar 20, and the belt 16 is slidingly secured to the receptacle 12 at open end 14 through hemmed portion 19. A free end of the belt 16 passes through the guide tube 18 in a proximal direction toward handle 24. The distal handle portion 60 is telescopically received completely over the guide tube 18, and the free belt end 26 then is secured within an inner end of the proximal handle portion 62, for example, using a set screw 64. The proximal handle portion 62 is telescopically received over guide tube 18 and the two handle portions 60 and 62 are interlocked together, for example, by manually press-fitting a reduced diameter end portion 66 of the proximal handle portion 62 into the distal handle portion 60.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. An instrument intended for percutaneous insertion through an access port for receiving, containing, and removing a specimen from a patient during a minimally invasive surgical procedure, the instrument including:
   a rigid, elongate guide member that has a proximal end and a distal end;
   an elongate belt that can be moved along the length of the guide member; has a proximal end outside the guide member; and has a belt portion that has a major axis and a minor axis, is more flexible to bending perpendicular to the plane of the major axis than to bending perpendicular to the plane of the minor axis, and forms a loop outside the distal end of the guide member when the proximal end of the belt is moved toward the guide member; and
   a receptacle that is connected to the belt, can be opened by moving the proximal end of the belt toward the guide member, and can be closed by moving the proximal end of the belt away from the guide member.

2. The instrument as defined in 1, further including a tubular sleeve that surrounds a portion of the guide member and is adapted to contain and initially direct the receptacle through the access port.

3. The instrument as defined in claim 1, in which the belt portion has an elliptical cross-sectional shape and is sufficiently rigid to allow it to be pushed through a central opening in the guide member for opening the receptacle.

4. The instrument as defined in claim 1, in which the belt portion is formed from nylon.

5. The instrument as defined in claim 1, in which the receptacle is formed from a waterproof nylon sheet material and includes securing means for slidably securing the receptacle to the belt.

6. The instrument as defined in claim 5, in which the receptacle has a hemmed portion of receptacle sheet material and the belt extends through the hemmed portion.

7. The instrument as defined in claim 1, in which the belt has a fixed end secured at the distal end of the guide member.

8. The instrument as defined in claim 7, in which the proximal end of the belt is secured to an actuating tube that is slidably telescoped over the proximal end of the guide member.

9. The instrument as defined in claim 7 further including a collar secured about the distal end of the guide member, the fixed end of the belt being secured between the guide member and the collar.

10. The instrument as defined in claim 9, in which a portion of the receptacle is secured to the guide member or to the collar.

11. The instrument as defined in claim 10, in which a second portion of the receptacle is secured to the guide member between the guide member and the collar.

12. The instrument as defined in claim 1, in which the guide member is a rigid hollow tube.

13. The instrument defined in claim 1, in which the belt portion is about twice as high as it is wide.

14. A surgical instrument for insertion in a patient to receive, contain, and remove a specimen, the instrument including:
   a receptacle bag for receiving and containing the specimen; and
   means for selectively opening or closing a mouth of the bag, the means including an elongate belt that has a major axis and a minor axis, is more flexible to bending perpendicular to the plane of the major axis, than to bending perpendicular to the plane of the minor axis, and can be activated from a location external to the patient to form a loop that is resistent to bending out of plane.

15. The surgical instrument as defined in claim 14, in which the belt is formed from nylon.

16. The surgical instrument as defined in claim 15, in which the belt is configured to transmit forces selectively in either direction along its longitudinal axis to selectively open or close the mouth of the bag.

17. The surgical instrument as defined in claim 14, in which the bag is formed from nylon.

18. The instrument defined in claim 14, in which a portion of the belt is about twice as wide as it is high.

19. A surgical instrument intended for percutaneous insertion through an access port for receiving, containing, and removing a specimen from a patient during a minimally invasive surgical procedure, the instrument including:
   a rigid, hollow guide tube with a proximal end and a distal end;
   a proximal handle portion adjacent the proximal end of the guide tube;
   a free end of an elongate belt passing through the guide tube and being secured within the proximal handle portion;
   an expanding portion of the elongate belt, the height of the expanding portion being more then 150% greater than the width of the expanding portion, and the expanding portion being moveable, upon movement of the proximal handle portion, between a retracted position within the guide tube and an extended position in the form of a planar loop outside the distal end of the guide tube, the plane of the loop being normal to the height of the expanding portion of the belt, and the loop being substantially more flexible to bending within the plane of the loop than to bending normal to the plane of the loop; and
   a specimen-retaining receptacle having an elongate, generally tubular, sealed bag and a mouth hemmed around the expanding portion of the belt, the receptable being openable by causing the expanding portion of the belt to be moved to the extended position, and being closeable by causing the expanding portion of the belt to be moved to the retracted position.

* * * * *